United States Patent
Kolluri et al.

(10) Patent No.: US 7,198,604 B2
(45) Date of Patent: Apr. 3, 2007

(54) METHOD AND SYSTEM FOR DETERMINATION OF PULSE RATE

(75) Inventors: Sai Kolluri, Tampa, FL (US); Lawrence T. Hersh, Tampa, FL (US); Richard Medero, Tampa, FL (US)

(73) Assignee: GE Medical Systems Information Technologies, Milwaukee, MI (US)

( * ) Notice: Subject to any disclaimer, the term of this patent is extended or adjusted under 35 U.S.C. 154(b) by 559 days.

(21) Appl. No.: 10/390,822

(22) Filed: Mar. 18, 2003

(65) Prior Publication Data

US 2004/0186386 A1 Sep. 23, 2004

(51) Int. Cl.
*A61B 5/00* (2006.01)

(52) U.S. Cl. .................. 600/490; 600/494; 600/496

(58) Field of Classification Search ............... None
See application file for complete search history.

(56) References Cited

U.S. PATENT DOCUMENTS

| 4,360,029 | A | 11/1982 | Ramsey, III | 128/681 |
|---|---|---|---|---|
| 4,543,962 | A | 10/1985 | Medero et al. | 128/682 |
| 4,638,810 | A | 1/1987 | Ramsey, III et al. | 128/681 |
| 4,796,184 | A | 1/1989 | Bahr et al. | 364/413.03 |
| 4,889,133 | A | 12/1989 | Nelson et al. | 128/681 |
| 4,949,710 | A | 8/1990 | Dorsett et al. | 128/680 |
| 5,518,000 | A * | 5/1996 | Booth et al. | 600/493 |
| 5,579,776 | A | 12/1996 | Medero | 128/680 |
| 5,704,362 | A | 1/1998 | Hersh et al. | 128/680 |
| 6,358,213 | B1 | 3/2002 | Friedman et al. | 600/493 |
| 6,423,010 | B1 | 7/2002 | Friedman et al. | 600/494 |
| 6,440,080 | B1 | 8/2002 | Booth et al. | 600/494 |
| 2002/0082507 | A1 | 6/2002 | Kolluri et al. | |
| 2004/0181157 | A1* | 9/2004 | Medero et al. | 600/500 |

* cited by examiner

*Primary Examiner*—Robert L. Nasser
(74) *Attorney, Agent, or Firm*—Andrus, Sceales, Starke & Sawall, LLP

(57) ABSTRACT

A method and system for determining pulse rate of a patient are disclosed. The method and system include acquiring measured information for at least one pulse at a pressure step, determining and storing quality values for the at least one pulse at the pressure step, analyzing pulse matching criteria for the pressure step, and determining pulse rate based on the measured information, quality values, and pulse matching criteria.

14 Claims, 8 Drawing Sheets

METHOD AND SYSTEM FOR DETERMINATION OF PULSE RATE

BACKGROUND OF THE INVENTION

The field of the invention is patient monitoring systems. More particularly, the invention relates to a patient monitoring method and system that determines blood pressure and pulse rate.

The heart muscles of humans periodically contract to force blood through the arteries. As a result of this pumping action, pressure pulses exist in these arteries and cause them to cyclically change volume. The maximum pressure that occurs at a location in an artery during a heart cycle is known as the systolic pressure and the minimum as diastolic pressure. These volume changes can be used to estimate oscillometric blood pressure values when measured with an applied pressurized cuff wrapped around the limb of a patient. From this information the oscillometric blood pressure is derived. Additionally, during the determination of an oscillometric blood pressure, it is desirable to make an estimate of the heart rate. If pulse period timing is gathered during the blood pressure determination, the pulse rate can be estimated.

There are different techniques and devices for measuring blood pressure and pulse rate values. One method in particular involves applying an inflatable cuff around an extremity of a patient's body, such as the patient's upper arm. The cuff is inflated to a pressure above the patient's systolic pressure and then reduced over time while a pressure sensor continues to measure the cuff pressure. The sensitivity of the sensor is such that pressure fluctuations within the cuff resulting from the beats of the patient's heart may be detected. With each beat there is a resulting small change in the artery volume which is transferred to the inflated cuff causing slight pressure variations within the cuff which are detected by the pressure sensor. The pressure sensor produces an electrical signal showing the cuff pressure and a series of small periodic variations associated with the beats of a patient's heart. These variations, called "complexes" or "oscillations," are used to determine the patient's blood pressure and pulse rate. This method of blood pressure and pulse rate determination is generally known as the oscillometric method.

Blood pressure measuring devices operating according to the oscillometric method detect the peak-to-peak amplitude of the pressure complexes at various applied cuff pressure levels. The amplitudes of these complexes, as well as the applied cuff pressure, are stored together as the device automatically changes the cuff pressures over a range of interest. The time period between the oscillations are often "filtered" or "averaged" to determine the pulse rate.

The reliability and repeatability of pulse rate computations hinges on the ability to accurately determine the complexes and their associated time period. Unfortunately, there are many barriers to accurately and reliably detecting and measuring oscillation characteristics, particularly the time period between the oscillations. For example, patient motion, vibrations, and other interference may cause artifacts in the pressure signal obtained from the cuff during blood pressure determinations. These artifacts are superimposed upon the desired oscillation signal, causing it to be distorted and making any timing measurements unreliable. It is often difficult to get two consecutive artifact free pulses. Furthermore, if the pulses are non-consecutive, determining the appropriate pulse period can be especially difficult. In order to provide greater patient comfort it is often desirable for blood pressure algorithms to take very little data at a single pressure step. Typically, oscillometric algorithms gather matched pulses at each pressure step. However, to accelerate a determination these same algorithms will change mode and take only a single pulse at some pressure steps. This forces these algorithms to try to compute pulse periods across pressure deflation steps. Oscillometric blood pressure determinations gather oscillations that are of different sizes depending on the applied cuff pressure. At times these pulse amplitudes may be so small compared to the artifact level that it is very difficult to get uncorrupted complexes and their associated timing. Pulse periods computed on low amplitude signals may output an inaccurate pulse rate. For these reasons, it is difficult to decide whether to publish blood pressure and pulse rate results or provide an indication that an accurate result is not possible with the given set of data. Therefore, there exists a need for a system and method to determine the quality and reliability of measured blood pressure data prior to making final determinations of a patient's actual blood pressure and pulse rate.

SUMMARY OF THE INVENTION

One embodiment of the present invention provides a method of determining a pulse rate of a patient including acquiring measured information for at least one pulse at a pressure step, determining and storing quality values for the at least one pulse at the pressure step, analyzing pulse matching criteria for the pressure step, and determining pulse rate based on the measured information, quality values, and pulse matching criteria.

Another embodiment of the present invention provides a method of determining pulse rate of a patient including determining pulse period data from pulses that meet predetermined criteria, wherein the predetermined criteria are selected so that a minimum number of pulse periods can be used to determine pulse rate. In addition, the method includes evaluating the pulse period data and determining the pulse rate from the pulse period data.

Another embodiment of the present invention provides an apparatus for determining a pulse rate of a patient including an inflatable cuff, a pressurizing apparatus coupled to the cuff for selectively applying pressure by inflating or deflating the cuff, and a cuff pressure sensor coupled to the cuff for sensing cuff pressure and blood pressure oscillations. In addition, the apparatus includes a programmed control device configured to control the pressure cuff and pressurizing apparatus, acquire measured information for at least one pulse at a pressure step, determine and store quality values for the at least one pulse at the pressure step, analyze matching criteria for the pressure step, and determine pulse rate based on the measured information, quality values, and pulse matching criteria.

Another embodiment of the present invention provides a system for determining a pulse rate of a patient including a means for acquiring measured information for at least one pulse at a pressure step, a means for determining and storing quality values for the at least one pulse at the respective pressure step, a means for analyzing matching criteria for the pressure step, and a means for determining pulse rate based on the measured information, quality values, and pulse matching criteria.

Another embodiment of the present invention provides a computer program product including a computer useable medium having computer logic for enabling at least one processor in a computer system to determine a pulse rate of a patient. In addition, the computer program product includes a means for acquiring measured information for at least one pulse at a pressure step, a means for determining and storing quality values for the at least one pulse at the pressure step, a means for analyzing matching criteria for the pressure step, and a means for determining pulse rate based on the measured information, quality values, and pulse matching criteria.

DESCRIPTION OF THE PREFERRED EMBODIMENT

Figure 1:
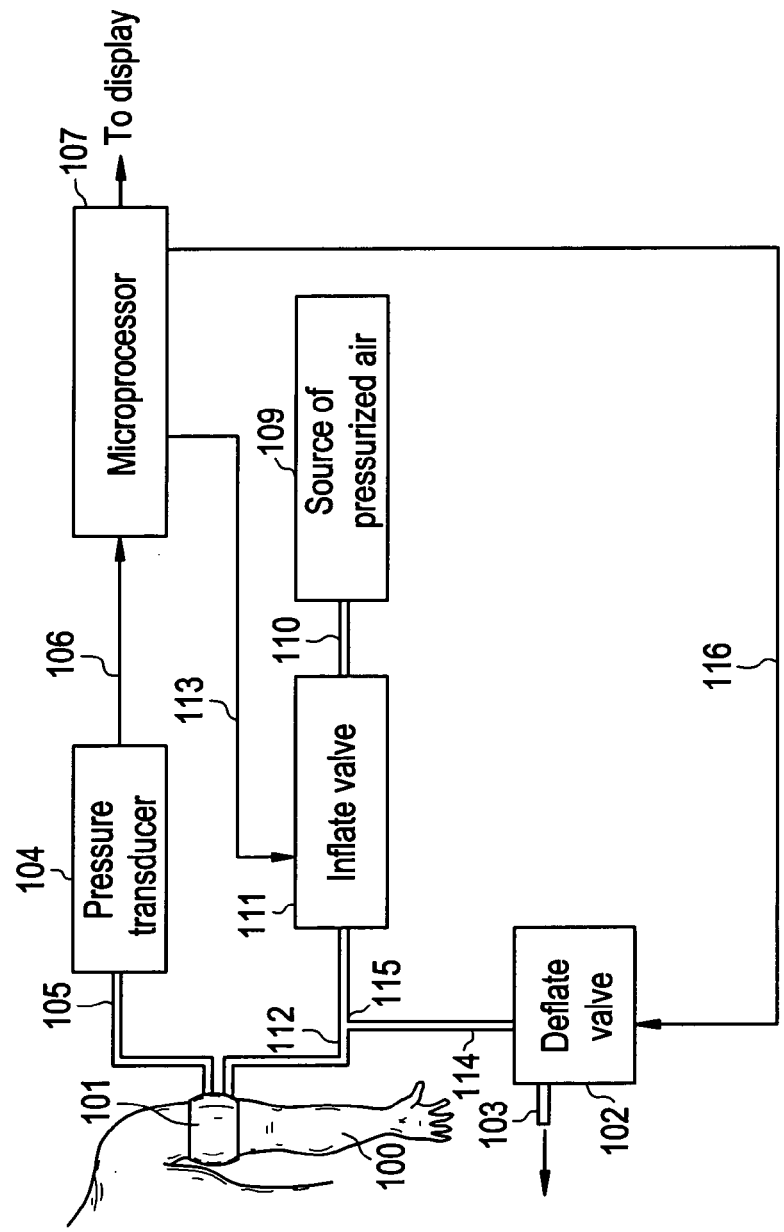
FIG. 1 is a diagram of a non-invasive blood pressure monitoring system in accordance with an embodiment of the present invention.

FIG. 1 shows the arm of a human subject wearing a conventional flexible inflatable and deflatable cuff 101 occluding the brachial artery when fully inflated. As cuff 101 is deflated using deflate valve 102 having exhaust 103, the arterial occlusion is gradually relieved. The deflation of cuff 101 via deflate valve 102 is controlled by microprocessor 107 via control line 116.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

Figure 2:
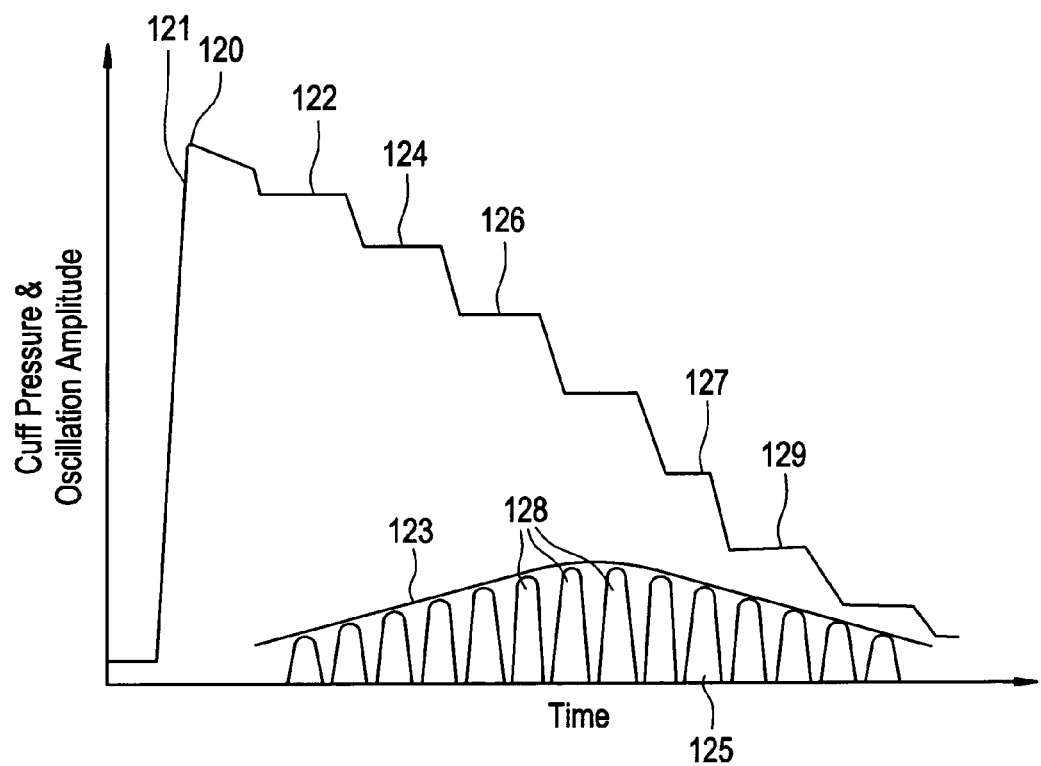
FIG. 2 displays typical waveforms for a normal oscillometric non-invasive blood pressure determination with cuff pressure and amplitude of oscillometric pulses shown as a function of time.

FIG. 2 displays typical waveforms for a normal oscillometric non-invasive blood pressure determination with amplitude of oscillometric pulses shown as a function of time. Two waveforms are shown. Curve 121 represents the overall cuff pressure of the inflatable cuff and curve 123 represents the measured oscillations in the cuff. As can be seen, the cuff is first inflated to a maximum pressure 120, and then reduced in a series of small incremental steps, such as steps 122, 124, 126. Oscillations 128 corresponding to each pulse are measured at each incremental cuff pressure. The peak pulse amplitudes (PPA) of each oscillation increases with each decrement of cuff pressure until the PPA reaches a maximum. As further deflation steps are taken past this maximum the PPA decreases. Deflations, since they take time, often prevent the acquisition of pulses as indicated by the measurement of oscillation 125 for step 127. Therefore the period calculation may need to find an accurate pulse rate using some non-consecutive pulses. When working across deflation steps the period found may need to be adjusted to take this problem into account as shown for the pulse at step 129. Although FIG. 2 shows incremental decreases in pressure steps, similar determinations as those above may also be made from continuous or linear decreases in pressure over time rather than incremental steps.

Figure 3A:
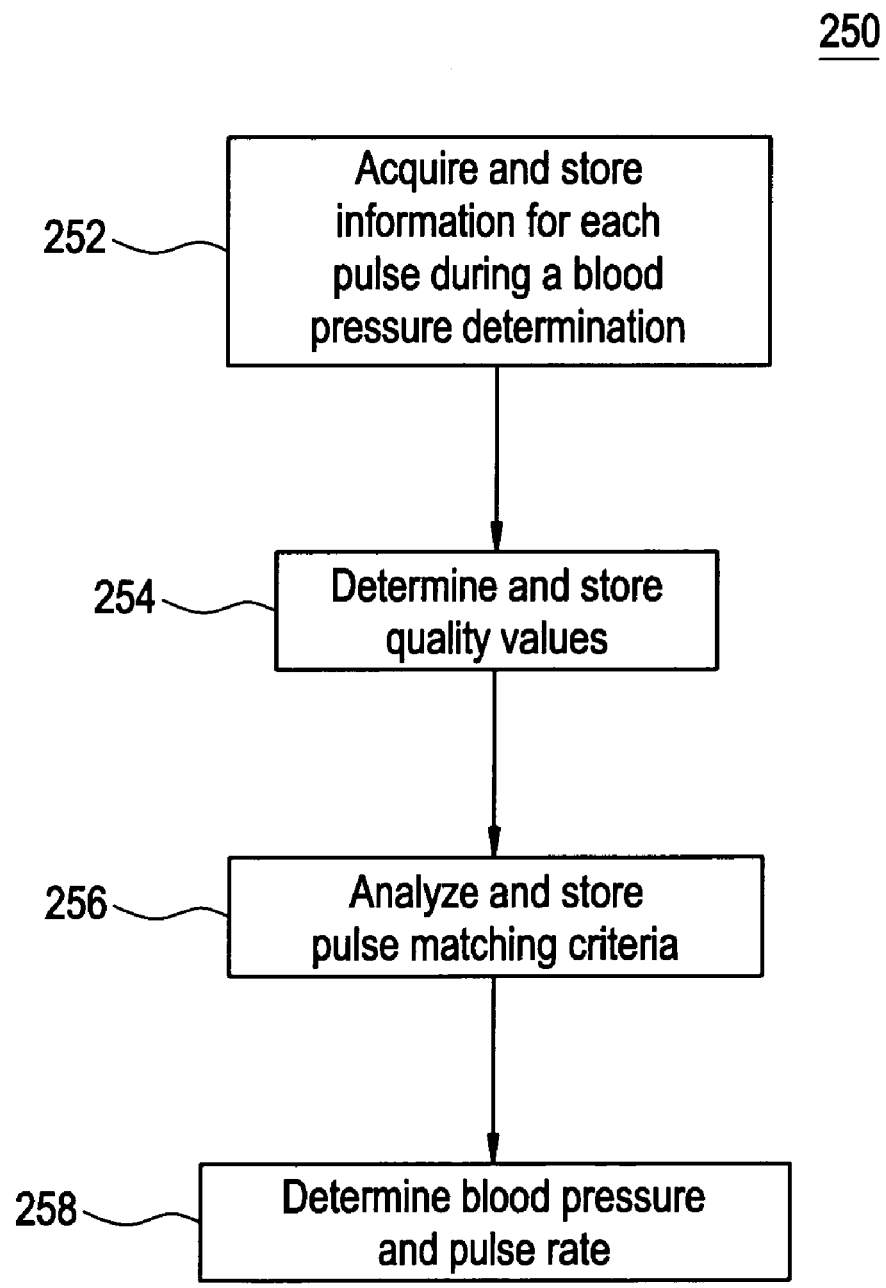
FIG. 3A is a flow chart of a portion of a process of pulse determination according to an embodiment of the present invention.

FIG. 3A shows a portion of a process for determining blood pressure and pulse rate of a patient according to an embodiment of the present invention. Specifically, FIG. 3A shows process 250 for determining blood pressure and pulse rate using various quality factors and information about different pulses. The process begins by determining and storing desired information for each pulse of the blood pressure determination at step 252. Step 254 includes determining and storing desired quality values, step 256 includes storing matching criteria, and step 258 includes determining blood pressure and pulse rate of a patient based on the information collected or derived in steps 252 through 256.

Figure 3B:
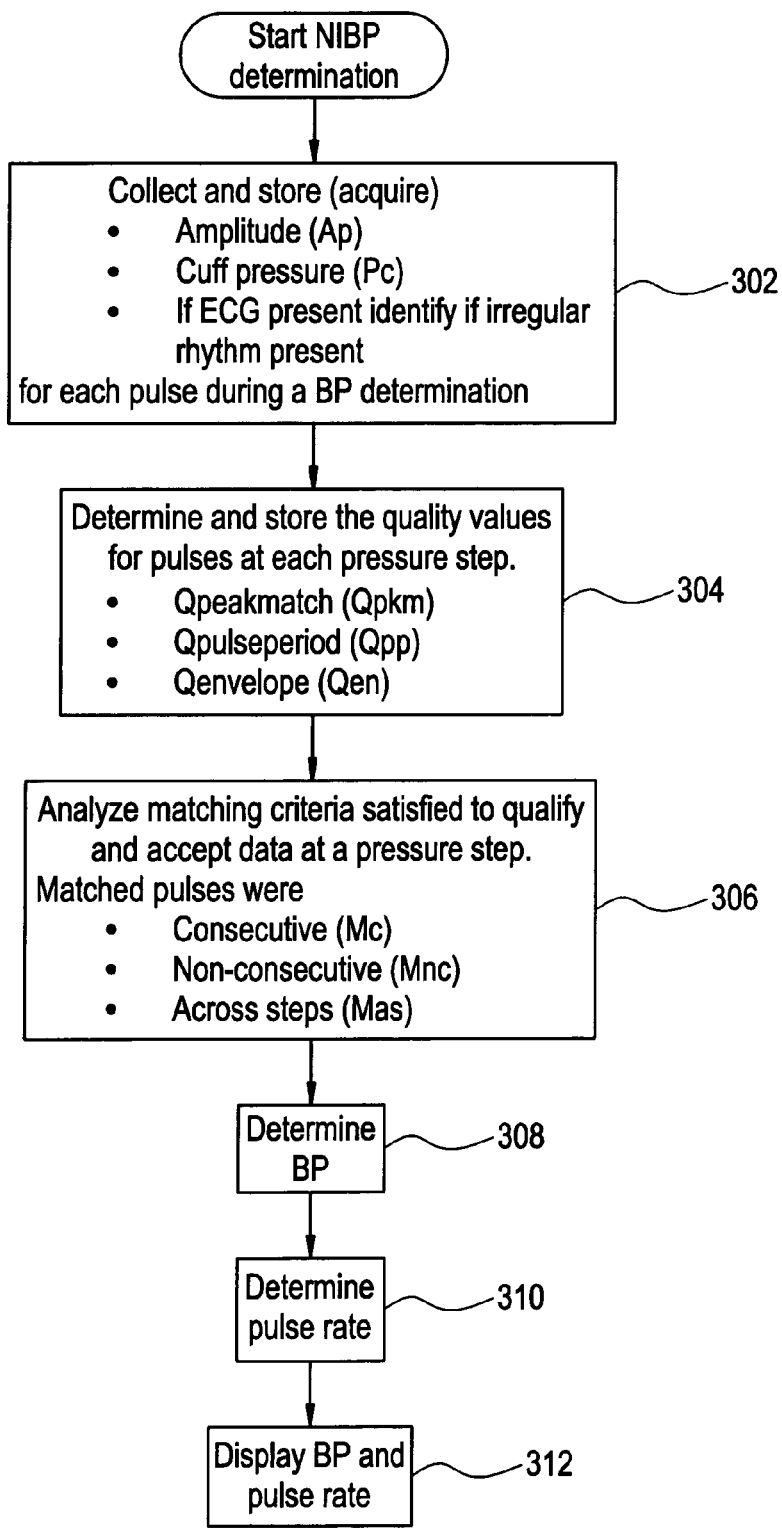
FIG. 3B is a flow chart of a portion of a process of pulse determination according to an embodiment of the present invention.

FIG. 3B shows a portion of a process for determining blood pressure and pulse rate of a patient according to an embodiment of the present invention. Specifically, FIG. 3B shows process 300 for determining blood pressure and pulse rate using various quality factors and information about different pulses. The first step of the process is to acquire particular measured information from each pulse during a blood pressure determination at step 302. Step 302 includes acquiring amplitude and cuff pressure data for each pulse during the blood pressure determination. At step 304, the process determines and stores a set of quality values (Q) based on measurements of various aspects of the pulses at each pressure step. The quality values include a peak match quality value, a pulse period quality value, and an envelope quality value. Each of these quality values will be discussed in detail below. After the quality values are determined, the process stores, at step 306, the matching criteria satisfied to qualify and accept data at pressure steps. The matching criteria describes if pulses were matched at a pressure step or a single pulse was acquired at a pressure step. If pulses were matched at a pressure step, matching criteria further describes if the matched pulses were consecutive or non-consecutive Next, the blood pressure is determined at step 308 and the pulse rate is determined at step 310. The blood pressure and pulse rate are then displayed at step 312.

The following discussion will address quality values in greater detail. Evaluation of a pulse as artifact occurs at two levels. The first is when complexes are collected and the second is when complexes are evaluated to produce blood pressure. The methods and quality factors associated with the complexes may also be used to produce a reliable pulse rate. Each measured feature of the pulse (or complex) has one or more associated quality values (Q), which are calculated using information from pulse samples of the current determination as well as information from a previous blood pressure determination. For example, measured features may include amplitude and pulse period. The associated quality factor measures may then be "Peak-Match-Quality" (or MPKQ), "Envelope-Quality" (or ENVQ) and "Pulse-Period-Quality" (or PPQ).

As the oscillometric blood pressure determination progresses, the quality values are updated and stored with the feature measurements. When the algorithm has collected enough samples to attempt to produce values, the pulse data, including the quality values, are evaluated to determine blood pressure and pulse rate. Some examples of quality functions are:

1. The Pulse Period Quality function (PPQ) is defined as:

$$PPQ(PP_1,PP_2)=100-(|PP_2-PP_1|\times 100/PP_1)$$

where $PP_1$ is a first pulse period, and $PP_2$ is a second subsequent pulse period. Note that this formula provides a number that can be easily used for the decision process.

2. The Peak Match Quality function (MPKQ) used to qualify pulse amplitudes at a cuff pressure is defined as:

$$MPKQ(PK_1,PK_2)=100-(|PK_2-PK_1|-3)\times 200/PK_1+PK_2)$$

where $PK_1$ is the amplitude of the first pulse, and $PK_2$ is the amplitude of the second pulse For many of the features that must be compared, a standard quality function can often be defined as:

$$Quality(X_1,X_2)=100-(|X_2-X_1|)\times 200/(X_1+X_2)$$

3. The definition of the Envelope Quality function (ENVQ) is more complicated because different comparisons of complex size need to be used for optimal algorithm performance. Essentially, the envelope quality is a comparison between a complex size and the value predicted for the complex size using the last curve fit, where a curve fit is found according to generally known principals in the art. The actual function used in the comparison changes at different stages of the envelope building process. In the process of computing an envelope quality the following four functions are used:

$$QNORM(X_1,X_2)=100-(|X_2-X_1|)\times 100/(X_1).$$

$$QADJ1(X_1,X_2)=100-(|X_2-2\times X_1|)\times 100/(2\times X_1).$$

$$QADJ2(X_1,X_2)=100-(|X_2-0.875\times X_1|)\times 100/(0.875\times X_1).$$

$$QADJ3(X_1,X_2)=100-(|X_2-1.125\times X_1|)\times 100/(1.125\times X_1).$$

For the ENVQ function $X_1$ is a complex size from a first complex obtained during the present determination, and $X_2$ is a complex size obtained from using a previous curve fit to predict complex size. The computation of envelope quality consists in first deciding which stage is applicable. Stage 1 of the ENVQ is used when the cuff pressure is above the systolic value, stage 2 is used when the cuff pressure is in the neighborhood of the MAP, and stage 3 is used for all other cuff pressure levels.

For stage 1 the $ENVQ(X_1, X_2)$ is:

If $X_1 \leq X_2$, THEN $ENVQ(X_1,X_2)=QNORM(X_1,X_2)$.

If $X_2 < X_1 \leq 2\times X_2$, THEN $ENVQ(X_1,X_2)=100$.

If $X_1 > 2\times X_2$, THEN $ENVQ(X_1,X_2)=QADJ1(X_1,X_2)$.

For stage 2 the $ENVQ(X_1, X_2)$ is:

If $X_1 \leq 0.5\times X_2$, THEN $ENVQ(X_1,X_2)=1$.

If $X_1 \geq 2\times X_2$, THEN $ENVQ(X_1,X_2)=1$.

If $0.5\times X_2 < X_1 \leq 0.875\times X_2$, THEN $ENVQ(X_1,X_2)=QADJ2(X_1,X_2)$.

If $0.875\times X_2 < X_1 < 2\times X_2$, THEN $ENVQ(X_1,X_2)=QADJ3(X_1,X_2)$.

For stage 3 the $ENVQ(X_1, X_2)$ is:

If $X_1 \leq 0.5\times X_2$, THEN $ENVQ(X_1,X_2)=1$.

If $X_1 \geq 2\times X_2$, THEN $ENVQ(X_1,X_2)=1$.

If $0.5\times X_2 < X_1 < 2\times X_2$, THEN $ENVQ(X_1,X_2)=QNORM(X_1,X_2)$.

Note that these formulas provides a number that can be easily used for the decision process. It should be noted that the quality values described above are merely exemplary. As one skilled in the art would appreciate, any number of variations of these as well as other quality values may be used.

Figure 4:
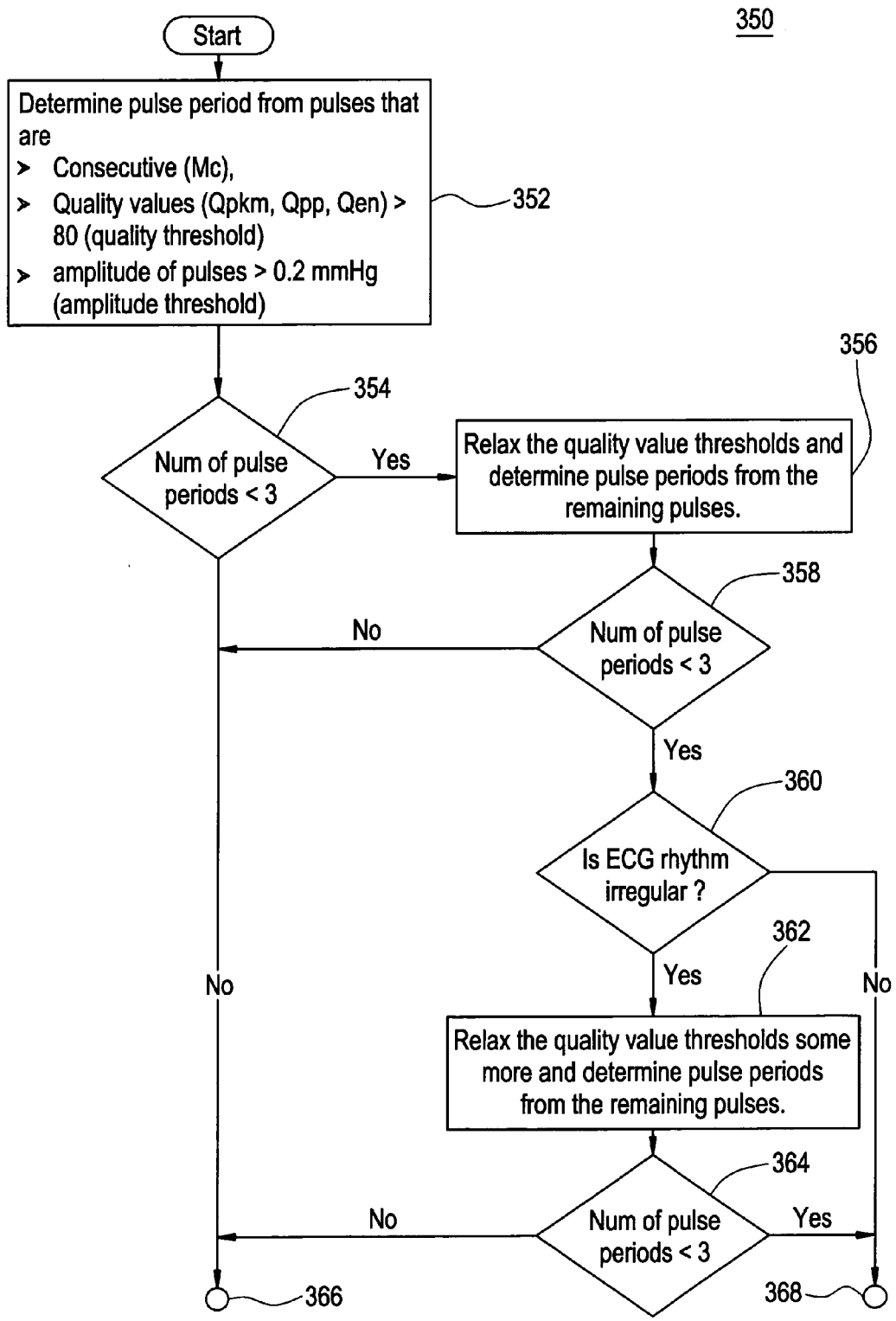
FIG. 4 is a flow chart of a portion of a process of pulse determination according to an embodiment of the present invention.

FIG. 4 shows a portion of process 350 for determining pulse rate according to an embodiment of the present invention. The process begins at step 352 by determining the pulse period from pulses that are consecutive, have quality values greater than a predetermined amount (e.g., 80), and have amplitudes greater than a threshold (e.g., 0.2 mm Hg). The quality values used at this step may include the peak match quality value, the pulse period quality value, and the envelope quality value. Of course, other quality values may be used for different embodiments. At step 354, the process determines whether there are less than three pulse periods. If there are less than three pulse periods (or some other minimum required number of pulse periods, e.g., 4, 5, etc.), the process proceeds to step 366 which will be described in FIG. 6. If there are less than three pulse periods, the process relaxes the quality value thresholds and determines pulse periods from the remaining pulses at step 356. In other words, if the quality value threshold had been 80 at step 352, the process could relax that threshold to a lower value (e.g., 70, 75, etc.). Further, the process may relax each individual quality value independently to a different value. For example, the peak match quality value could be 75 and the pulse period quality value could be 70. As one skilled in the art can appreciate, any number of variations in quality values can be used at this step. The essential idea is that the criteria are relaxed or changed from a very rigorous level to a very loose level until some pulses have met the quality requirements at a particular level and are available for use in the pulse period calculation. In this way it is insured that the pulse period is calculated with the best possible data, even in noisy situations. Of course, for some data sets the quality requirements for any level are not met and the pulse period cannot be determined at all. This will eventually lead to step 480 of FIG. 6 with no pulse rate output. After relaxing the quality values, if the number of pulse periods is not less than three at step 358, the process continues to step 366 which is also described in FIG. 6. If there are less than three pulse periods at step 358, the process proceeds to step 360 where the ECG signal is measured for irregularities. If there is not an irregular ECG rhythm, the process proceeds to step 368 which is described in more detail on FIG. 5. If there is an irregular ECG rhythm, the quality values are further relaxed at step 362 so that pulse periods are determined from the remaining pulses. The number of pulse periods are once again measured at step 364. The ECG signal is just one possible source for establishing (or qualifying) heart rhythm irregularities and then relaxing certain quality factors to compensate. Other sources such as a plethysmograph signal from a pulse oximetry sensor may also be used to compensate for heart irregularity and relaxation of quality factors. If the number of pulse periods is then less than three, the process proceeds to step 368 on FIG. 5. If the number of pulse periods is not less than three, the process proceeds to step 366 on FIG. 6.

Figure 5:
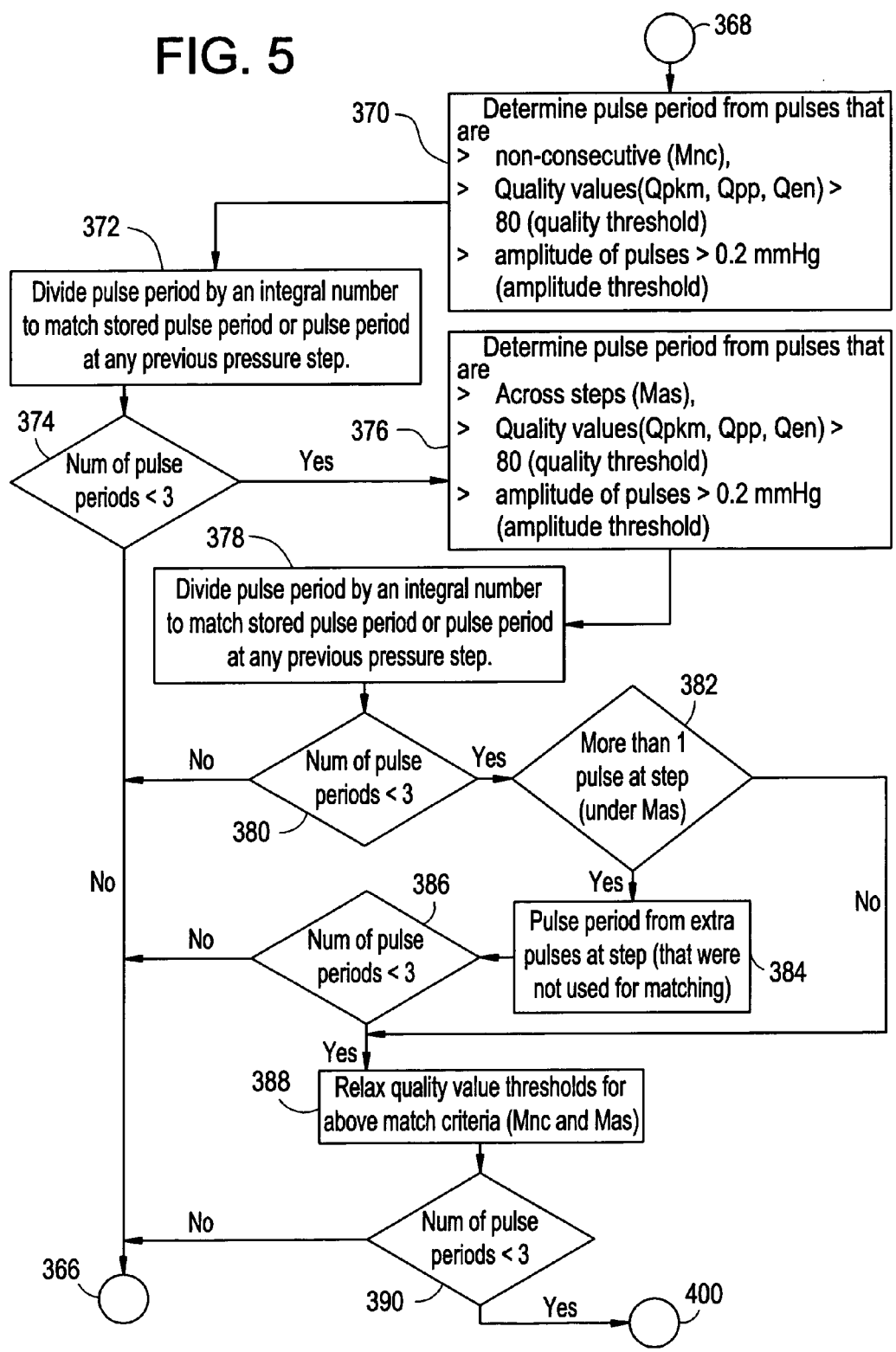
FIG. 5 is a flow chart of a portion of a process of pulse determination according to an embodiment of the present invention.

FIG. 5 shows a portion of process 350 for determining pulse rate according to an embodiment of the present invention. The process begins at step 368 when there are less than the minimum required number (three in this case) of pulse periods in the current blood pressure determination. Step 370 initiates the determination of pulse period from pulses that are non-consecutive, have quality values greater than a predetermined amount (e.g., 80), and have amplitudes greater than a threshold (e.g., 0.2 mm Hg). At step 372, the pulse periods from the non-consecutively matched pulses are, if possible, divided by an integral number to match a stored pulse period from a previous blood pressure determination on the same patient or a pulse period from any previous pressure step in the current blood pressure determination. In the event that there is not a pulse period from a previous determination on the same patient or pulse period from a previous pressure step in the current blood pressure determination, a pulse period from an ECG or other sensor may be used to match the pulse period. Otherwise these pulses cannot be used to compute the pulse period. At step 374, the process determines whether the number of pulse periods is less than three. If the number of pulse periods is not less than three, the process proceeds to step 366 on FIG. 6. If there are less than three pulse periods, the process proceeds to step 376.

At step 376, the process determines pulse periods from pulses that are across steps, have quality values greater than a predetermined amount (e.g., 80), and have amplitudes greater than a threshold (e.g., 0.2 mm Hg). The quality values used at this step may include the peak match quality value, the pulse period quality value, and the envelope quality value. Of course, other quality values may be used for different embodiments. At step 378, the pulse periods are divided by an integral number to match a stored pulse period from a previous determination on the same patient or a pulse period from any previous pressure step or other sensors. At step 380, the process determines whether the number of pulse periods is less than three. If the number of pulse periods is not less than three, the process proceeds to step 366 on FIG. 6. If the number of pulse periods is less than three, the process proceeds to step 382 where a determination is made as to whether there is more than one pulse at a pressure step when the algorithm is in a mode where it only is trying to accept a single pulse to qualify the data for computation of blood pressure. The need for acquisition of these additional pulses may be due to the presence of artifact and an indication that these pulses are not good for use in calculating blood pressure. However, these pulses may still be adequate for establishing pulse period. If there is not more than one pulse, the process proceeds to step 388. If there is more than one pulse, the process determines the pulse period from the extra pulses (i.e., that were not used for calculating blood pressure) at step 384. After the pulse period is determined, the process determines whether the number of pulses is less than three at step 386. If the number is not less than three, the process proceeds to step 366 on FIG. 6. If the number is less than three, the process relaxes the quality value thresholds that were used at steps 370 and 376 and determines the pulse periods at step 388. The process then determines whether the number of pulse periods is less than three at step 390. If the number is less than three, the process proceeds to step 400. If the number is not less than three, the process proceeds to step 366 of FIG. 6.

Figure 6:
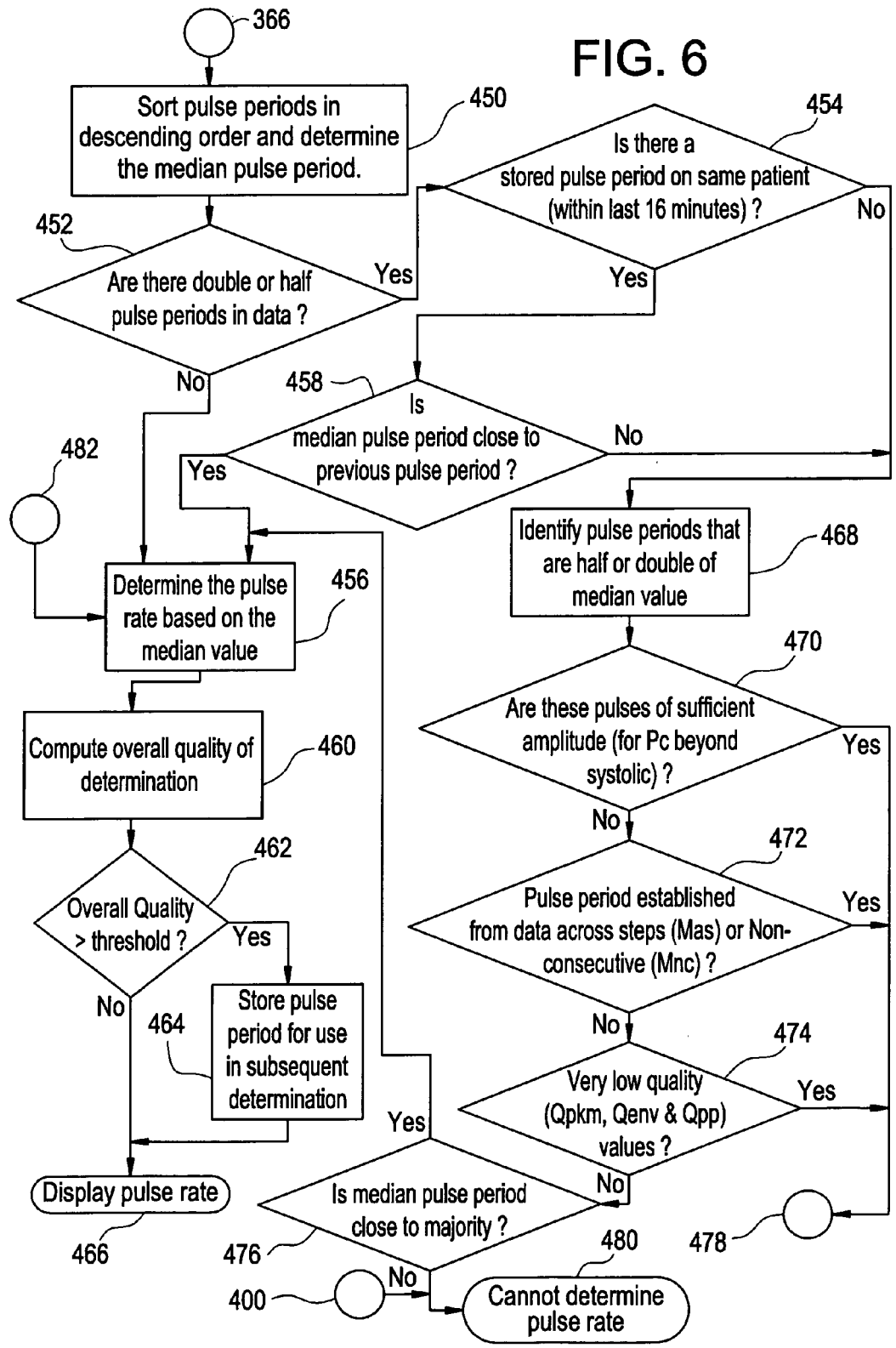
FIG. 6 is a flow chart of a portion of a process of pulse determination according to an embodiment of the present invention.

FIG. 6 shows a process for determining pulse rate beginning with step 366 after obtaining a sufficient number of data points (e.g., at least 3 points). The process begins by sorting pulse periods in descending order and determining the median pulse period at step 450. At step 452, the process determines whether there are any half and/or double pulse periods in the data. For example, the process looks for a data point that is either about half or double the median pulse period. If there is not a half or double data point, the process proceeds to step 456. At step 456, the process determines the pulse rate based on the median value. After the median is determined, the process determines the overall quality of the determination at step 460. For example, a method for an overall quality of determination computation is described in U.S. Pat. No. 6,358,213 to Friedman et al. The process then determines whether the overall quality is greater than the threshold at step 462. If the overall quality is greater than the threshold, the process stores the pulse period for use in a subsequent determination at step 464. If the overall quality is not greater than the threshold, the process displays a pulse rate at step 466. Similarly, a pulse rate is displayed after step 464.

Referring back to step 452, if there are double and/or half pulse periods in the data, the process proceeds to step 454 where it is determined whether there is a stored pulse period on the same patient within a predetermined period of time (e.g., 16 minutes). If there is a stored pulse period on the same patient within the predetermined period of time, the process proceeds to step 458. At step 458, the process determines whether the median pulse period is close to the previous pulse period. If so, the process proceeds to step 456. If the median pulse period is not close to the previous pulse period, the process proceeds to step 468. A pulse period is close to the previous pulse period if the pulse rate from the current pulse period is within about 10 beats/minute (BPM) of the previous pulse rate. It should be noted that this measure is merely exemplary and any number of other comparisons may be made to determine whether the pulse period is close to the previous pulse rate. If there was not a stored pulse period on the same patient within a predetermined period of time at step 454, the process proceeds to step 468. At step 468, the process identifies pulse periods that are half and/or double the median value. Steps 470, 472, 474 evaluate the underlying reason for having half or double the median pulse period data. At step 470, the process determines whether the pulses that are identified at step 468 are of sufficient amplitude (e.g., for cuff pressure beyond the systolic pressure, the amplitudes are small and may have passed through the relaxed criteria in any of the above described methods). If so, the process proceeds to step 478 on FIG. 7. If the pulses are not of sufficient amplitude, the process determines, at step 472, whether the pulse period was established from non-consecutively matched pulses at the same pressure step or from pulses that were gathered across two different pressure steps. If so, the process proceeds to step 478. Otherwise, the process determines at step 474 whether the data is of poor quality because the quality factor thresholds were relaxed in any of the above-described methods. If so, the process proceeds to step 478. If the underlying reason for having double or half the median pulse period data cannot be established, the process determines whether the median pulse period is close to the majority of pulses at step 476 (i.e., does the median pulse period have a pulse period close to the average pulse period of the majority of pulses). If so, the process proceeds to step 456. If not, the process proceeds to step 480 and cannot determine pulse rate.

Figure 7:
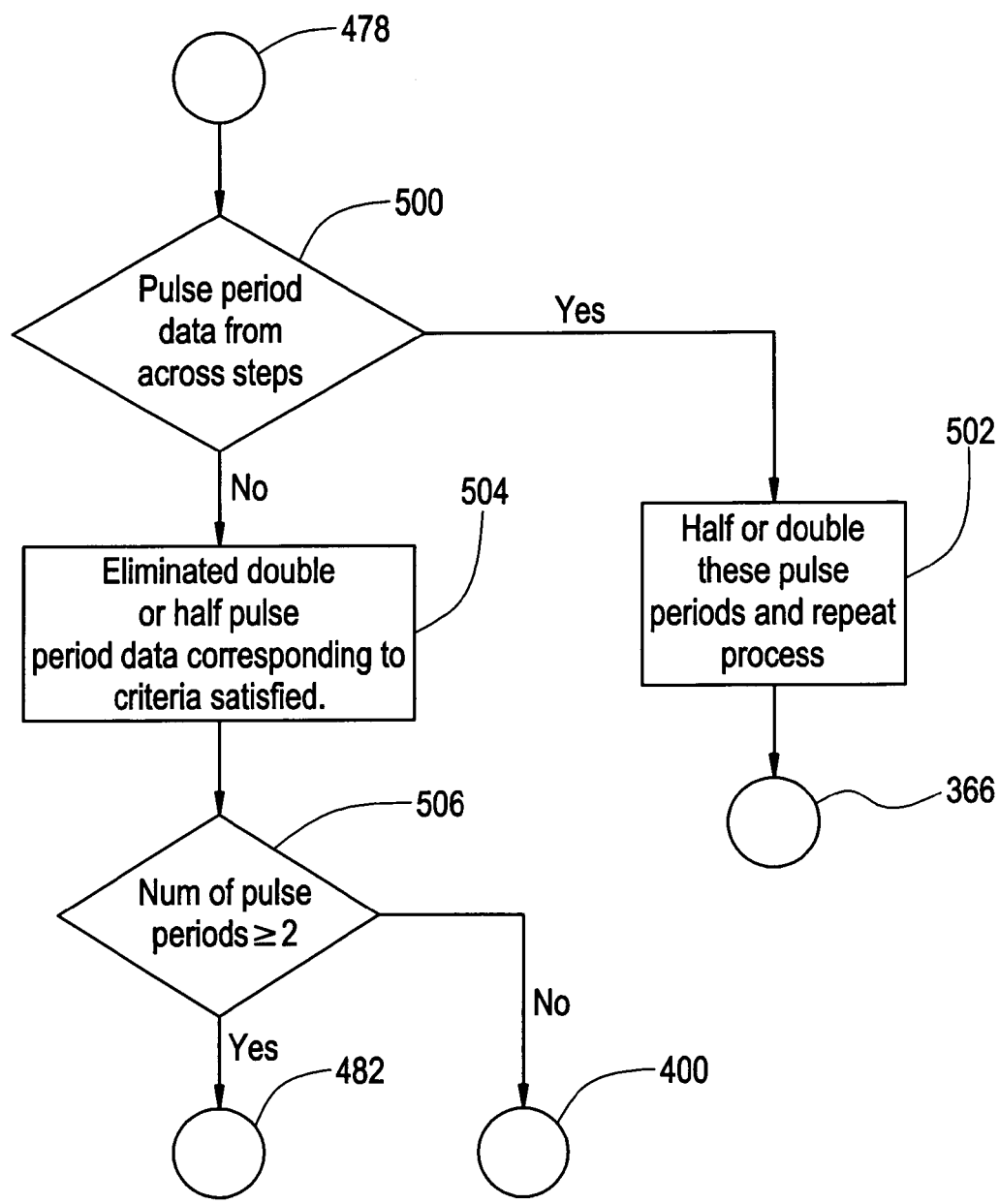
FIG. 7 is a flow chart of a portion of a process of pulse determination according to an embodiment of the present invention.

FIG. 7 shows a portion of a process for determining pulse rate according to an embodiment of the present invention. Specifically, FIG. 7 shows process 478 where the underlying reason for having double or half the median pulse period has been established and may very well be due to criteria that have been relaxed to the extent of producing poor data results. At step 500, the process determines whether the pulse period data is from across steps. If so, the process arbitrarily doubles or divides the pulse periods in half at step 502 to match the median pulse period and, the process proceeds to step 366 on FIG. 6. Referring to step 500, if the pulse period data is not from pressure pulses across steps, the process eliminates all of the double or half pulse period data at step 504 (may be due to signal being of low amplitude or poor quality factors). For example, if the data is from low amplitudes and non-consecutive matching, then the data point may be removed. At step 506, the process determines whether there are at least two pulse periods left. If so, the process proceeds to step 482 on FIG. 6. If not, the process proceeds to step 400 on FIG. 6.

It should be noted that the amplitude threshold to qualify a pressure pulse in the processes described above may be different for adult patients and neonatal patients. For example, different cuffs may be applied depending on the particular situation and patient. Depending on the cuff used, different information can be obtained from the measurements and limits imposed thereon. Therefore, it should be understood that variations of the examples and figures discussed in this application are contemplated to work in a variety of situations.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A method of determining a pulse rate of a patient comprising: acquiring and storing measured information for at least one pulse at each of a plurality of pressure steps;
   determining and storing quality values for the at least one pulse at each of the plurality of pressure steps;
   analyzing pulse matching criteria for the plurality of pressure steps;
   selecting measured information from a set of pulses that have quality values greater than a predetermined amount and meet a pulse matching criteria; and
   determining the pulse rate based on the selected measured information.

2. The method of claim 1, wherein acquiring measured information for one or more pulses at each of the pressure steps comprises determining at least one of the following measurements: (a) amplitude, (b) cuff pressure, and (c) presence of an irregular rhythm.

3. The method of claim 2, wherein determining and storing quality values for one or more pulses at each of the pressure steps comprises calculating at least one of the following: (a) a peak match quality value, (b) an envelope quality value, and (c) a pulse period quality value.

4. The method of claim 3, wherein analyzing matching criteria for the plurality of pressure steps includes evaluating criteria for qualifying data for at least one of the following types of matched pulses: (a) consecutive, (b) non-consecutive, and (c) across step.

5. The method of claim 4, wherein pulse periods are determined from pulses that have quality values greater than a predetermined amount and amplitudes greater than a threshold amount.

6. The method of claim 4, further comprising displaying pulse rate.

7. The method of claim 1, further comprising determining blood pressure based on quality values and matching criteria.

8. An apparatus for determining the pulse rate of a patient comprising:
   an inflatable cuff;
   a pressurizing apparatus coupled to the cuff for selectively applying pressure by inflating or deflating the cuff;
   a cuff pressure sensor coupled to the cuff for sensing cuff pressure and blood pressure oscillations;
   a programmed control device configured to control the pressure cuff and pressurizing apparatus, acquire and store blood pressure oscillations for at least one pulse at each of a plurality of pressure steps, determine and store quality values for the at least one pulse at each of the pressure steps, analyze matching criteria for the plurality of pressure steps, and determine pulse rate based on the blood pressure oscillations meeting a threshold for quality value, and meeting a pulse matching criteria.

9. The apparatus of claim 8, wherein the blood pressure oscillations that the programmed control device is configured to acquire includes at least one of the following measurements: (a) pulse amplitude, (b) cuff pressure, and (c) presence of an irregular rhythm.

10. The apparatus of claim 9, wherein the programmed control device is configured to determine and store quality values including at least one of the following quality values: (a) a peak match quality value, (b) an envelope quality value, and (c) a pulse period quality value.

11. The apparatus of claim 10, wherein the programmed control device is configured to evaluate pulse matching criteria for at least one of the following types of matched pulses: (a) consecutive, (b) non-consecutive, and (c) across step.

12. The apparatus of claim 11, wherein the programmed control device is further configured to display pulse rate and determine blood pressure based on the blood pressure oscillations, quality values, and matching criteria.

13. A system for determining a pulse rate of a patient comprising:
   means for acquiring and storing measured information for at least one pulse at each of a plurality of pressure steps;
   means for determining and storing quality values for the at least one pulse at each of the plurality of pressure steps;
   means for analyzing matching criteria for the plurality of pressure steps; and
   means for determining pulse rate based on the measured information, quality values, and pulse matching criteria.

14. A computer program product comprising:
   a computer readable medium having computer logic for enabling at least one processor in a computer system to determine a pulse rate of a patient;
   means for analyzing and storing measured information for at least one pulse at each of a plurality of pressure steps;

means for determining and storing quality values for the at least one pulse at each of the plurality of pressure steps;

means for analyzing matching criteria for the plurality of pressure steps; and means for determining pulse rate based on the measured information, quality values, and pulse matching criteria.

* * * * *